United States Patent [19] [11] 3,996,326
Schachet [45] Dec. 7, 1976

[54] METHOD OF EMBEDDING A HISTOLOGY SPECIMEN

[75] Inventor: Eli Schachet, St. Louis, Mo.

[73] Assignee: Sherwood Medical Industries Inc., St. Louis, Mo.

[22] Filed: Apr. 9, 1975

[21] Appl. No.: 566,507

Related U.S. Application Data

[63] Continuation of Ser. No. 379,892, July 26, 1973, abandoned.

[52] U.S. Cl. .................. 264/158; 264/271; 264/275; 264/294; 264/299; 264/330
[51] Int. Cl.² ................ B29C 5/00; B29C 17/08
[58] Field of Search .......... 264/271, 299, 157, 158, 264/219, 274, 275, 349, 238, 294, 330; 206/46 R, 84; 229/44 R; 425/117

[56] References Cited

UNITED STATES PATENTS

| | | | |
|---|---|---|---|
| 2,996,762 | 8/1961 | McCormick | 264/271 |
| 3,234,595 | 2/1966 | Weichselbaum et al. | 425/117 |
| 3,456,300 | 7/1969 | Pickett | 425/117 |
| 3,674,396 | 7/1972 | McCormick | 425/117 |

OTHER PUBLICATIONS

Humason, Animal Tissue Techniques, W. H. Freeman & Co., San Francisco (1972) p. A2.

Primary Examiner—Willard E. Hoag
Attorney, Agent, or Firm—Stanley N. Garber; William R. O'Meara

[57] ABSTRACT

A method of providing a specimen section embedded in a section of paraffin wax includes providing a mold having a cover and upper and lower portions with a body of solidified paraffin wax therein, heating the paraffin wax while in the mold until it becomes molten, removing the cover of the mold, placing a specimen in the liquid paraffin in the lower mold portion, cooling the paraffin until it becomes a hardened body, and removing the lower mold portion to provide a hardened block of paraffin secured to the upper mold portion with a lower end portion extending below the lower end of the upper mold portion and containing the embedded specimen. The upper mold portion with the paraffin block is disposed within a microtome so that one or more slices of the hardened paraffin block may be cut therefrom to provide a slice of the block which includes a section of the embedded specimen.

14 Claims, 6 Drawing Figures

METHOD OF EMBEDDING A HISTOLOGY SPECIMEN

This is a continuation, of application Ser. No. 379,892, filed July 26, 1973, and now abandoned.

BACKGROUND OF THE INVENTION

This invention relates to specimen embedding devices and methods of forming specimen containing embedding medium blocks from which sections of the specimen may be cut for analysis.

Generally, in order to provide a specimen section, such as a histological tissue specimen, for mounting on a microscope slide, the specimen is embedded in a block of an embedding medium, such as paraffin wax, and then separate sections or slices of the block and specimen are cut from the block by a cutting device, such as a microtome. In the past, the specimen was placed in the bottom of a mold having an upper open end and molten paraffin was poured into the mold to cover the specimen. After the paraffin solidified into a block, it was removed from the mold, and then sliced by a microtome to provide specimen sections which may be placed on slides for microscopic analysis. U.S. Pat. No. 2,996,762 describes a method in which a lower mold part is removed from the solidified paraffin containing the specimen while an upper mold part remains with the paraffin for clamping in a microtome. The method of this patent, however, requires the handling of bulk embedding medium, such as paraffin wax. This, in turn, requires paraffin melting and holding implements which are relatively expensive, necessitates the pouring or dispensing of melted paraffin into each specimen containing mold at the hospital or laboratory, subjects the material to foreign matter, and generally requires careful and skilled technicians. Such methods also generally result in heating excessive paraffin and also necessitate laboratory clean-up.

SUMMARY OF THE INVENTION

It is therefore an object of the present invention to provide an improved specimen embedding device and method of embedding specimens wherein the above-mentioned disadvantages are substantially obviated.

Another object is to provide an improved specimen embedding device that requires no pouring or dispensing of liquid paraffin at the point of use.

Another object is to provide a specimen embedding material supply container and molding device which is easy to use and does not require auxiliary melting and pouring or dispensing apparatus to provide a specimen embedded in a body of embedding material.

Another object of the present invention is to provide a novel method of embedding specimens in embedding medium blocks for slicing to provide specimen sections for analysis purposes which generally minimizes the skills and time required, and avoids clean-up problems usually encountered in past processes.

Still another object is to provide a supply package prefilled with a predetermined amount of solidified specimen embedding material wherein at least portions of the package are used as molding elements in producing a molded body of material having a specimen embedded therein.

In accordance with one aspect of the present invention, a specimen embedding material supply container and molding device is provided which includes a mold having an upper mold portion with an upper open end and a lower mold portion having a closed bottom end. A solidified mass of specimen embedding material is provided within the mold which is meltable within the mold upon the application of heat thereto, and the lower mold portion is separable upon solidification of the embedding material to provide an exposed lower end portion of the solidified embedding material containing the specimen. In accordance with another aspect, the upper mold is closed at the top by a removable cover to seal the interior of the mold and solidified body of embedding material against foreign matter. In accordance with another aspect of the invention a method for embedding a specimen is provided which includes providing a mold having upper and lower portions with a solidified body of meltable specimen embedding material therein, applying heat to melt the embedding material therein, inserting a specimen into the molten material with the specimen moved into the lower mold portion, solidifying the material within the mold, and removing the lower mold portion to expose a solidified lower portion of the embedding material with the specimen embedded therein.

These and other objects and advantages of the present invention will become apparent from the following detailed description and accompanying drawing.

DESCRIPTION OF THE PREFERRED EMBODIMENT

Figure 1:
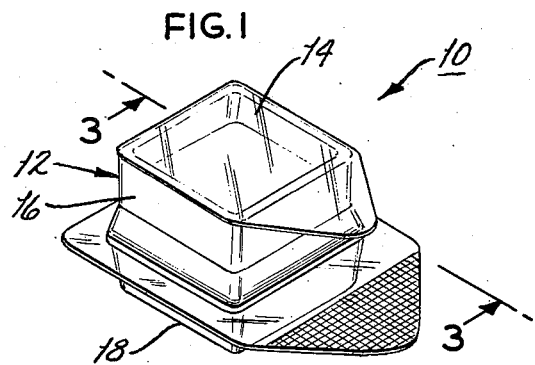
FIG. 1 is a perspective view of a specimen embedding material supply container and molding device in accordance with one embodiment of the present invention.

Referring now to the drawing, there is shown in FIG. 1 a specimen embedding material supply container and molding device 10 including a mold 12 having a peelable or removable cover member 14 attached to the top of the mold. The mold 12 includes an upper mold portion 16 and a lower mold portion 18. As better seen in FIGS. 2 and 3, the mold 12 is prefilled with a predetermined amount of solidified specimen embedding material 20. Embedding material 20 is normally paraffin wax such as conventionally used in embedding specimens, for example, in the process of providing tissue specimen sections for microscopic studies, such as histological studies.

Figure 3:
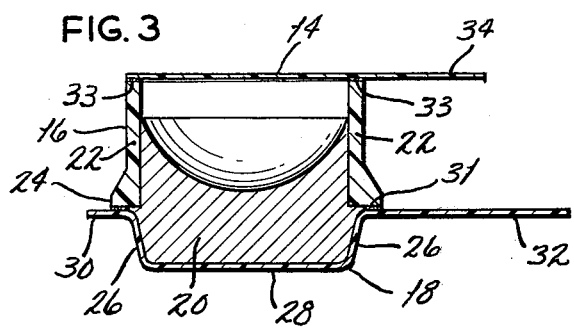
FIG. 3 is a cross-sectional view taken along line 3—3 of FIG. 1.

The upper mold portion 16 is shown generally rectangular in shape having two pairs of opposed parallel side walls 22 arranged to provide a generally square tube which is open at the upper end as well as at the lower end (FIG. 3). The upper mold portion is provided with a peripheral radially outwardly extending lower flange 24. The mold portion 16 is relatively rigid and maintains its shape in use. It may be formed of any suitable material, for example, a plastic, such as polytherphthalate, polypropylene, or a relatively hard styrene, and may be formed in any suitable manner, depending upon the material used, for example, it may be molded, such as by injection molding, or by blow molding.

The lower mold portion 18 is shown generally cup-shaped including four side walls 26 arranged in generally rectangular form, and a substantially flat bottom wall 28 closing the lower end of the mold portion. The upper end of mold portion 18 is open and is provided with a peripheral radially outwardly extending flange 30. The lower mold portion 18 is shown connected to the upper mold portion 16, for example, by providing a suitable adhesive 31 between the flanges 24 and 30. Preferably, adhesive 31 is of a type which will provide an adequate seal between the mold portions 16 and 18 to prevent the embedding material or paraffin 20, when molten, from leaking out of the mold, but will not prevent relatively easy separation of the upper and lower mold portions. The adhesive 31 may be, for example, an elastomeric adhesive or rubber base cement, which is preferably of the non-hardening type. The adhesive preferably should be capable of holding the mold portions 16 and 18 in sealed relation while the mold is subjected to the temperatures normally encountered during use of the device. It is desirable that the adhesive 31 have a low peel strength with at least one of the mold portions 16 and 18 to permit removal thereof. In some cases, instead of adhesive, the mold portions may be designed to snap or lock together in fluid tight relation with or without cement.

The lower mold portion 18 is further provided with a handle or tab 32 connected to the flange 30 which may be an integral extension thereof, as shown in the drawing. Tab 32 serves as a means for grasping the lower mold portion and readily disconnecting it from the molded paraffin 20 and the upper mold portion 16, as will be discussed more fully herein. The lower mold portion 18 is formed of a material whereby it will maintain its shape at the usual temperatures encountered during use but is sufficiently flexible to permit relatively easy removal thereof by pulling on the tab 32 in a direction away from the upper mold portion when the paraffin 20 is in a solid condition. It may be made of any suitable material, for example, it may be made of the same material as portion 16, or of another suitable plastic material, or of a metal such as aluminum foil. Lower portion 18 is preferably formed such that it is more flexible or pliable than upper mold portion 16 for easy removal without damage to the molded paraffin. It is shown as being formed from a thin plastic material which is substantially thinner than that of the upper mold portion 16.

In assembling the embedding material supply container and molding device 10, the upper and lower mold portions 16 and 18 of mold 12 are preferably secured together by adhesive 31, and a solidified body of embedding material 20 is disposed in the mold. For example, a predetermined amount of paraffin may be placed in the mold by pouring molten paraffin therein to a predetermined level, such as the level shown in the drawings, and then allowing it to cool and harden. Alternately, a desired amount of solid paraffin may be deposited in the mold.

The cover 14 may be a thin sheet, for example, a flexible elastomeric film which does not undesirably degrade upon heating to the melting temperature of the paraffin. Cover 14 may be, for example, a Mylar or a vinyl film. The cover is secured by a suitable adhesive 33 which may be of the same material as adhesive 31. Adhesive 33 may be applied to the upper end of the upper mold portion, as indicated in FIGS. 1 and 3. The cover 14 is shown having an integral tab or handle 34 to facilitate the removal or peeling thereof from the top of the upper mold portion 16 at the time of use. The adhesive 33 should permit relatively easy removal of the cover 14 from the upper mold portion 16 without spilling the molten paraffin. The cover seals the mold so that the paraffin is stored in the sealed interior or chamber of the mold 12 and prevents foreign particles from entering the mold during storage, and thus prevents such particles from entering the paraffin when melted. It is, of course, important to prevent any foreign matter from entering the mold since such might interfere with microscopic studies.

Figure 4:
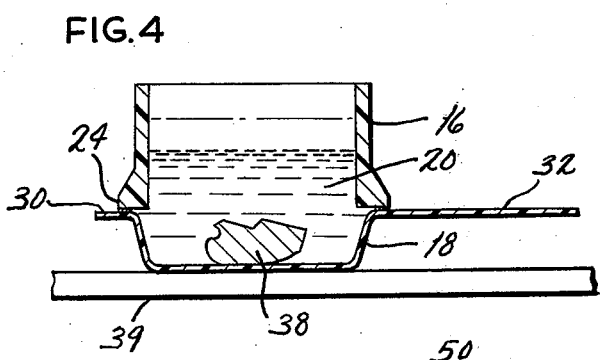
FIG. 4 is a view similar to FIG. 3 but illustrating a step in the method of embedding a specimen in the embedding material.

In the process of embedding a specimen, for example, a tissue specimen for histological studies, an embedding material supply container and molding device 10 is heated in any suitable manner to melt the paraffin. For example, the device 10 may be placed in a heated atmosphere such as in an oven, to melt the normally solid body of embedding paraffin 20 within the mold 12. The supply of paraffin 20 in the prefilled mold 12 is such that when molten, it completely fills the lower mold portion 18 and extends upwardly in the upper mold portion 16 to a level whereby the upper mold portion will support the paraffin 20 when it is subsequently hardened into a solid block or body and the lower mold portion is removed. For example, the molten paraffin may extend upwardly about half-way into the upper mold portion 16 as shown in FIGS. 3 and 4. The cover 14 is removed either before or after the paraffin has been melted to open the upper end of the portion 16 and mold 12 to provide access to the interior of the mold and paraffin therein. The specimen, indicated at 38 in FIG. 4, is then placed in the molten paraffin and orientated as desired in the lower mold portion, and the paraffin allowed to cool and harden.

Preferably, the cover 14 is removed or partially removed from the mold 12 after paraffin 20 has been melted within the container where the mold with molten paraffin is to be handled or moved in order to avoid the danger of spilling molten paraffin. Also, the mold 12 is preferably placed on a heated surface or hot table, such as indicated at 39 in FIG. 4, to maintain the paraffin in a molten condition while performing the above orientation of the specimen. After the desired specimen orientation, the cooling of the paraffin may be assisted by placing the mold 12 on a cold plate.

After the paraffin 20 has been solidified with the specimen 38 embedded therein, the tab 32 and upper mold portion 16 may be hand grasped and pulled apart to remove the lower mold portion 18 from the solidified block of paraffin and the upper mold portion. Since the paraffin extends upwardly into the upper mold portion 16, it adheres to the side walls of the upper mold portion so that the upper mold portion securely holds the block of paraffin 20. The lower mold portion 18, while providing sufficiently rigid side walls 26 to contain and mold the paraffin, is sufficiently flexible, as previously mentioned herein, to be readily removed from the lower end of the upper mold portion 16 and the block of solidified paraffin without damage to the lower end of the paraffin block.

With the lower mold portion 18 removed, the relatively rigid upper mold portion 16 serves as a holder for carrying the solid paraffin wax block with the specimen embedded therein. The mold portion 16 and block of paraffin 20 are positioned in a microtome, such as indicated at 40 in FIG. 5, which may be of any suitable or conventional well-known design. The microtome 40 is shown having a pair of opposed clamping members 42 and 44 which engage one pair of the opposed parallel flat side walls 22 of the rectangular mold portion 16 to firmly clamp the mold portion in the microtome. The mold is then accurately postioned under a knife, indicated at 48, which is adapted to cut through the molded paraffin block and the specimen embedded therein.

Figure 2:
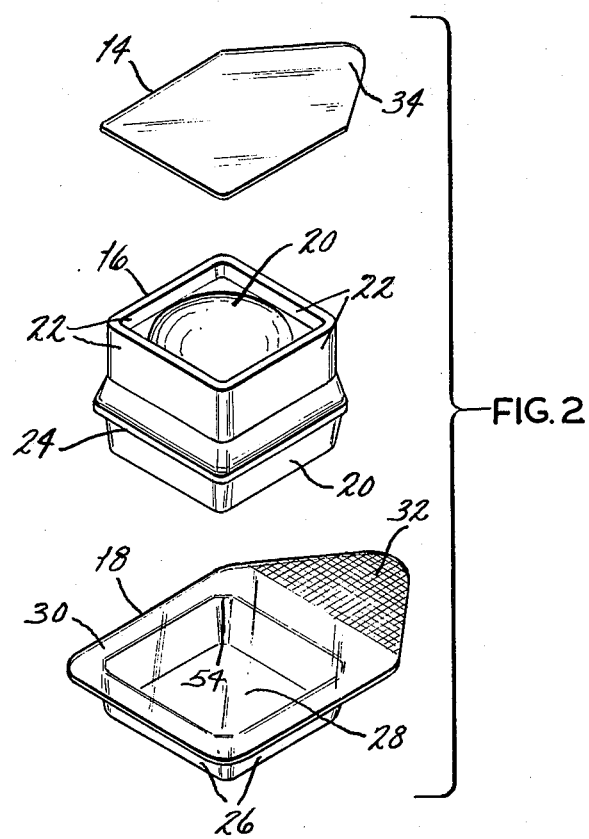
FIG. 2 is an exploded view of the device of FIG. 1.
Figure 6:
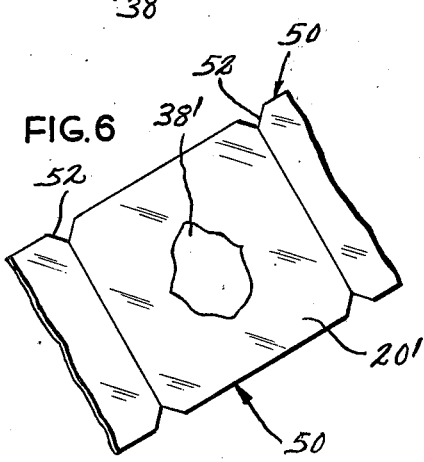
FIG. 6 is a perspective view of a slice from the block of embedding material shown in FIG. 5.
Figure 5:
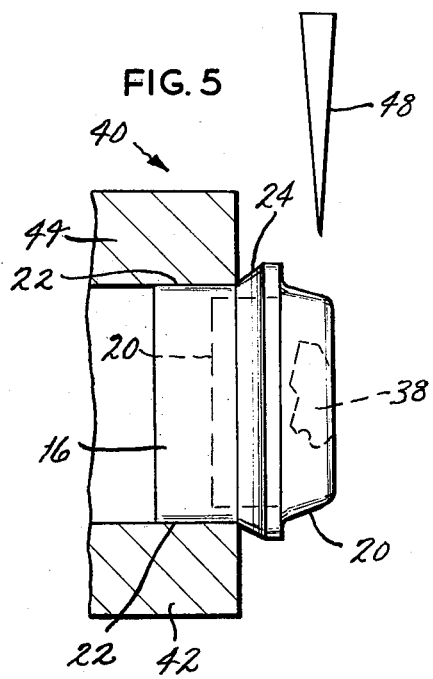
FIG. 5 is a plan view showing a block of embedding material with a specimen embedded therein and disposed in a microtome.

In FIG. 6 there is shown several slices, indicated at 50, which were produced by the slicing operation indicated in FIG. 5. Each slice includes a section of paraffin indicated at 20', and a section of the specimen indicated at 38'. One or more slices 50 may be cut from the paraffin block containing the embedded specimen. The block, with the remaining portion of the paraffin wax and specimen, where desired, may be stored for reference purposes. Successive slices 50 are readily separated without breaking by providing flats 52 at each corner of the slice; these flats being the result of providing the lower mold portion 18 with axially extending flat corners 54 (FIG. 2). The adjacent flats 52 form notches between adjacent sections 20' which aid in separating the sections. Each slice 50, as is well known, may be attached to a conventional transparent microscope slide (not shown) and, where desired, subjected to various treatments. The specimen on the slide may then be covered by a coverslide and positioned in a microscope for microscopic analysis.

The embedding device 10 thus serves as a prefilled embedding material supply container or package that also serves as a mold, and provides an effective device in the method of embedding specimens. It will be apparent that handling time is reduced and the apparatus for handling and pouring bulk paraffin at the time of embedding specimens is eliminated by use of the present prefilled package and embedding device, and the method of embedding as described above is simple and effective. It will be apparent that the time required to perform the above embedding process may often be greatly reduced as compared to processes requiring the handling of bulk specimen embedding materials, where the length of time can be critical where histological analysis is involved. Also, as previously mentioned herein, the present invention avoids waste and substantially reduced the amount of clean-up normally required when bulk paraffin is used at the embedding station. Furthermore, the danger of foreign particles or airborne matter entering the embedding material is reduced since the supply of embedding material, in the embodiment shown, is sealed in the container chamber by adhesive 33 and cover 14 until the time of use. Also, no measuring and inadvertent under or over filling occurs with the device and method of the present invention since a desired predetermined amount of material is disposed in the supply package 10.

While there has been shown and described preferred forms of the invention herein, it will be understood that various changes and modifications thereto may be made without departing from the true spirit and the scope of the invention as set forth in the appended claims.

What is claimed is:

1. A method of embedding a histological tissue specimen in embedding material for use in preparing a section of the specimen for microscopic analysis comprising the steps of providing a mold having an upper mold portion with upper and lower open ends, and a lower mold portion having an open upper end and a closed lower end, a body of solidified meltable specimen embedding material disposed in said mold, and cover means connected to the mold closing the upper end of the upper mold portion to prevent the entrance of foreign matter into the mold, with the solidified embedding material opening the upper end portion of the mold to permit access to the interior of the mold, heating the embedding material while in the mold to melt the same to a liquid, thereafter placing a specimen into the melted embedding material adjacent the closed end of said lower mold portion, cooling the embedding material to solidify the same, and removing said lower mold portion from the solidified embedding material to provide a block of embedding material adhering to said upper mold portion with a lower portion of said block extending from the lower end thereof and having the specimen embedded therein.

2. The method of claim 1 wherein said beating step includes simultaneously heating both said mold and said embedding material.

3. The method of claim 2 wherein said heating step includes heating the mold with embedding material therein in a heated atmosphere.

4. The method of claim 2 wherein the embedding material is paraffin wax.

5. A method of embedding a histological tissue specimen in embedding material for use in preparing a section of the specimen for microscopic analysis comprising the steps of providing a mold having an open upper end and a closed lower end, a body of solidified meltable specimen embedding material sliceable by a microtome disposed in the mold, and cover means connected to the mold closing said upper end for preventing the entrance of foreign matter into the mold with the solidified embedding material, opening said upper end to permit access to the interior of the mold, heating the embedding material while in the mold to melt the same to a liquid, thereafter inserting from the exterior of the mold a specimen in the melted embedding material in the mold, cooling the embedding material to solidify the same and form a block of solidified embedding material having the specimen embedded therein, and then removing at least a portion of the mold from the block to expose at least a portion of the block.

6. The method of claim 5 wherein the embedding material comprises paraffin so that a slice can be cut from said block which contains a section of the specimen.

7. The method of claim 5 wherein said step of heating the embedding material precedes said step of opening said upper end.

8. A method of making a section of a histological tissue specimen for microscopic analysis comprising the steps of providing a mold having an open upper end and a closed lower end, a body of solidified meltable specimen embedding material disposed in the mold, and cover means connected to the mold closing said upper end for preventing the entrance of foreign matter into the mold, with the solidified embedding material opening said upper end to permit access to the interior of the mold, heating the embedding material while in the mold to melt the same to a liquid, positioning a specimen in the melted embedding material in the mold, cooling the embedding material so solidify the same and form a block of solidified embedding material having the specimen embedded therein, then removing at least a portion of the mold from the block to expose at least a portion of the block, and cutting a slice from the block which contains a section of the specimen.

9. The method of claim 8 wherein said embedding material comprises paraffin, and said cutting step includes clamping and cutting said block in a microtome.

10. The method of claim 8 wherein the specimen is inserted through said upper open end of the mold and into the embedding material after the embedding material is in liquid form.

11. The method of claim 8 wherein said step of opening said upper end is subsequent to said step of heating the embedding material.

12. The method of claim 8 wherein said step of opening said upper end comprises removing said cover means from said mold.

13. The method of claim 8 wherein said step of providing said cover means comprises connecting said cover means to the mold after the body of solidified meltable specimen embedding material is disposed in the mold.

14. A method of making a section of a tissue specimen for microscopic analysis comprising the steps of providing a specimen embedding material supply container and molding device comprising an upper supply container portion defining an upper mold portion open at the upper and lower axial ends thereof and having axially extending side walls, a lower supply container portion defining a lower mold portion having a bottom wall closing the lower end thereof and an upper open end connected with the lower end of said upper mold portion, a body of a predetermined amount of solidified meltable specimen embedding material disposed within the supply container and molding device, and a removable cover sealingly closing the upper open end of said upper mold portion to prevent the entrance of foreign matter into the mold with the solidified embedding material, said lower mold portion being removable from said upper mold portion and said embedding material when said embedding material is in a solidified condition to provide an exposed lower end portion of the solidified embedding material that extends axially below the lower end of said upper mold portion, removing said cover, heating said container and molding device to melt the embedding material therein, inserting a specimen through the open end of the mold and into the lower mold portion while the embedding material is molten, orientating the specimen relative to the plane of said bottom wall, thereafter allowing the embedding material within the mold to cool and solidify to form a block of embedding material with a specimen embedded in the bottom portion thereof, removing the lower mold portion from the solidified embedding material and said upper mold portion, clamping said upper mold portion in a microtome, and cutting a slice from the bottom portion of the block of embedding material in a plane generally parallel to the plane of the end of the bottom of the block to provide a slice of the block with a section of the specimen embedded therein.

* * * * *